United States Patent [19]

Staver

[11] 4,217,908
[45] Aug. 19, 1980

[54] VECTOR LEAD APPARATUS AND METHODS OF CONSTRUCTING AND UTILIZING SAME

[75] Inventor: Peter J. Staver, Lincoln Park, Mich.

[73] Assignees: Bernard B. Staver; Margaret Staver, both of Baraboo, Wis. ; part interest to each

[21] Appl. No.: 951,610

[22] Filed: Oct. 16, 1978

[51] Int. Cl.³ .............................................. A61B 5/04
[52] U.S. Cl. .................................................... 128/643
[58] Field of Search ............... 128/643, 639, 783, 802, 128/803, 299–301

[56] References Cited

U.S. PATENT DOCUMENTS

| 2,580,628 | 1/1952 | Welsh | 128/643 |
| 2,619,278 | 11/1952 | Ackerman | 128/300 X |
| 3,534,733 | 10/1970 | Phipps et al. | 128/643 |
| 3,640,270 | 2/1972 | Hoffmann | 128/643 |
| 3,783,865 | 1/1974 | Ricketts | 128/643 |

FOREIGN PATENT DOCUMENTS

| 2208653 | 4/1973 | Fed. Rep. of Germany | 128/643 |
| 2815 | of 1911 | United Kingdom | 128/301 |

Primary Examiner—Lee S. Cohen
Attorney, Agent, or Firm—Irving M. Weiner; Pamela S. Burt; Melvin Yedlin

[57] ABSTRACT

The invention provides electrical connectors used in the field of medical electrocardiography, and provides a connecting device which is universally adaptable to electrocardiography machines, and eliminates the need to apply electrically conductive gels to an area of the skin by providing a disposable contact with an electrically-conductive sponge. The disposable contact is held in place within a substantially rigid vacuum bell, with a pliable rubber ring which distorts to form an airtight seal between the vacuum bell and a patient's skin.

14 Claims, 4 Drawing Figures

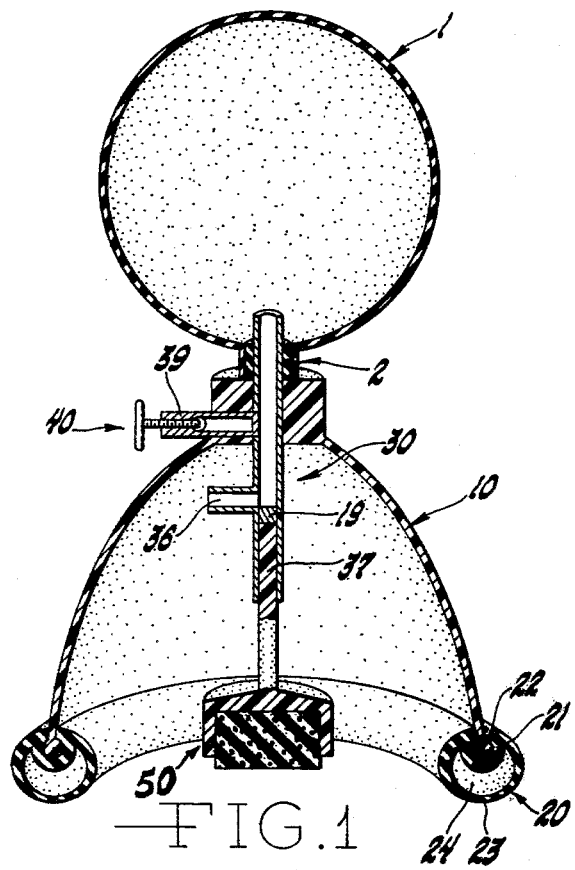
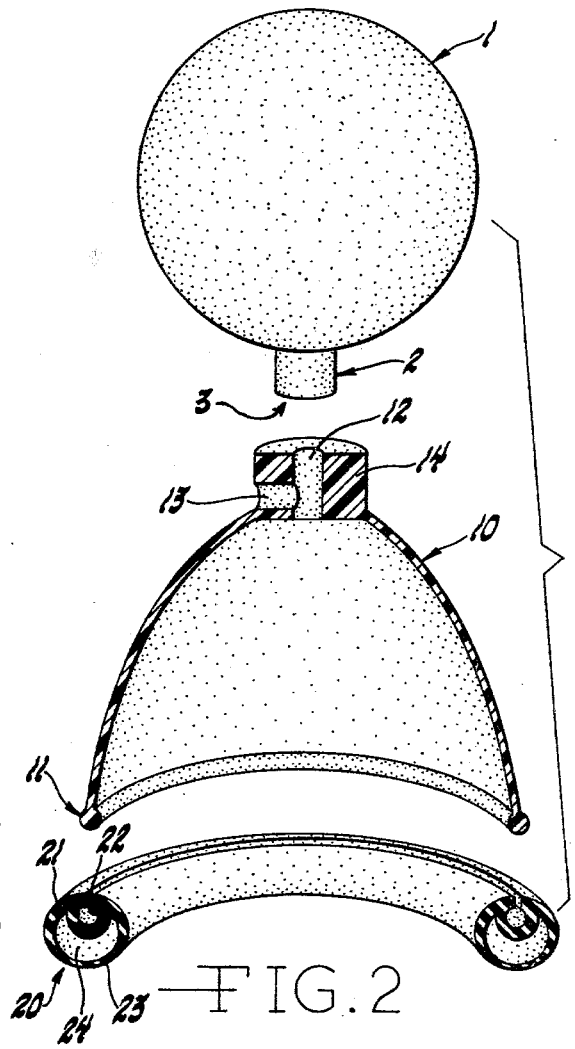
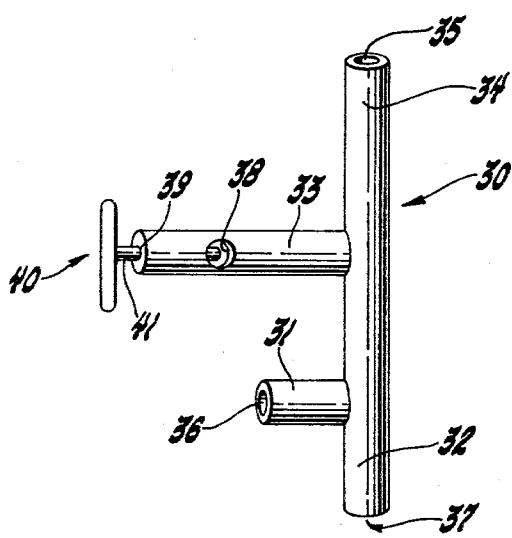
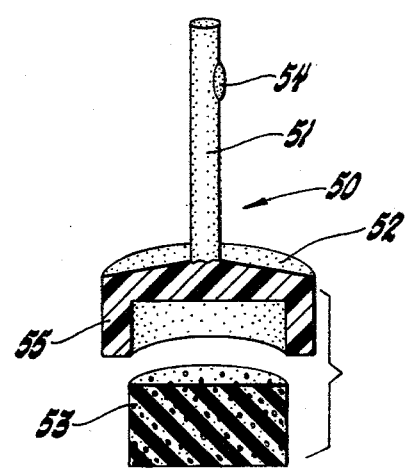

VECTOR LEAD APPARATUS AND METHODS OF CONSTRUCTING AND UTILIZING SAME

The present invention relates generally to novel medical instrumentation electrode apparatus, novel contact members, and to novel medical instrumentation kits.

BACKGROUND OF THE INVENTION

The invention relates primarily to the field of medical electrocardiography, involving connecting wiring between the surface of a human body and an electrocardiograph (EKG) machine for measuring and recording the electrical waveforms emitted by a human heart, for purposes of detecting, diagnosing and treating heart ailments. The wires involved are known as Vector Leads, and are attached to a human body in various ways, such as flat metallic plates taped in place, or by a conductive suction cup. These plates and suction cups are put in place after an area of the skin has been coated with a conductive jelly to insure good electrical contact.

There have been numerous different approaches to the problem of attaching electrical wires to the skin surface of a human or other mammal, such as those disclosed in U.S. Pat. Nos. 3,534,733 and 3,976,055, and German Auslegeschrift No. 2,208,653.

U.S. Pat. No. 3,534,733, issued in 1970 to Phipps et al, entitled "SPRING-LOADED SUCTION CUP-TYPE BIOMEDICAL INSTRUMENTATION ELECTRODE", discloses a device for attaching a co-axial cable from biological instrumentation equipment to the skin of an underwater cetacean, such as a porpoise, which is free to move about. The Phipps device comprises a large suction cup, with a spring-loaded contact pad at its center. The body surface and the spring-loaded contact, which may include a sponge disc impregnated with conductive gel, are coated with a conductive gel before the device is put in place.

U.S. Pat. No. 3,976,055, issued in 1976 to Monter et al, entitled "ELECTRODE AND CONDUCTOR THEREFORE", discloses a method of making normally non-conductive materials conductive by the addition of conductive particles to the material, and insuring good electrical contact with conductive gel applied to the electrode and skin surface by provision of a small contact area of galvanically-active material. Monter discloses a cup-shaped member of this conductive material, to be retained by the vacuum created by a suction bulb, and to be used with the conductive gel applied to the electrode or the skin surface. It can be connected to pin-tipped vector leads.

German Auslegeschrift No. 2,208,653, issued in 1973 to Heyne, discloses a suction-retained electrode, including a large sponge pad impregnated with a conductive gel, and a flexible vacuum bell. As in the Phipps patent, the conductive pad is an integral part of the assembly. The Heyne device is usable only with an external vacuum source, and has an electrical wire which is located inside a tube connected to the vacuum source.

In contradistinction to the present invention, no known prior art device usable as a Vector Lead electrode is adaptable to any currently-used-conventional EKG machine, nor eliminates the time consuming, messy application of conductive gel, nor has a disposable contact member together with a reusable retaining and support member.

SUMMARY OF THE INVENTION

The present invention has for its principal object the provision of a vacuum-retained Vector Lead electrode device which is universally adaptable to all currently-used EKG machines and which eliminates the need for application of electrically-conductive gels to an area of the skin by providing a disposable contact.

Another object of the present invention is to improve the contact of the electrode with the skin by the provision of a resilient ring at the base of the device.

Another object of the present invention is to provide a single contact electrode together with a single size retaining device to obviate the need for retaining devices in a plurality of sizes.

Another object is to provide a disposable contact electrode which is inexpensive to manufacture and easy to use.

Another object is to provide a disposable contact electrode which reduces the time necessary for connecting Vector Leads to human skin.

BRIEF DESCRIPTION OF THE DRAWINGS

FIG. 1 illustrates a Vector Lead apparatus, partially in section, according to the present invention as viewed in its functioning position.

FIG. 2 is a view showing the non-conductive or electrically-insulating portions of the Vector Lead apparatus according to the present invention.

FIG. 3 is a view showing the electrically-conductive portions of the Vector Lead apparatus.

FIG. 4 is a view of a disposable contact electrode.

DETAILED DESCRIPTION

FIG. 1 illustrates the assembly of a first possible embodiment of the instant invention with a bulb 1, a bell 10, a stem 30, a ring 20 and a disposable contact 50 in operating position.

FIG. 2 illustrates the non-conductive, electrically-insulating portions of the instant invention. The bulb 1 may be formed or fabricated from a conventional rubber or elastomeric material, and may be of sufficient size to cause or produce a partial vacuum within the bell 10. The bulb 1 may have a neck 2, with an aperture 3 which is oriented substantially co-axially with the neck 2 to tightly retain the stem 30, and to form an airtight seal between the stem 30 and the neck 2.

The bell 10 may be made of a conventional electrically-insulating material, such as, for example, a polyvinyl chloride plastic. The bell 10 may be substantially rigid, but should still possess sufficient resiliency to allow installation of the stem 30, and to form an airtight seal between the stem 30 and the bell 10.

The bell 10 may be provided with a rim 11 to retain ring 20. Bell 10 has apertures 12 and 13 in neck 14 to receive stem 30.

The ring 20 may preferably, but not essentially, be made of a soft, pliable material, such as latex rubber. The ring 20 may preferably, but not essentially, be formed with a substantially heavy section 21, and an aperture 22 adapted to receive the rim 11.

The ring 20 may be provided with a thin, pliable section 23, forming an aperture 24, so that the ring 20 can collapse against a patient's skin and form an airtight seal therewith. The ring 20 may preferably, but not essentially, be fabricated in a substantially straight section of appropriate length, and then made into a ring using suitable adhesives, such as cyanoacrilate adhesives.

In the preferred embodiment of the present invention, the bell 10 is approximately one inch in diameter adjacent to the rim 11, and one and one-half inches in height.

FIG. 3 illustrates the conductive stem 30, in an exterior view. Reference is also made to the sectional view of FIG. 1 for certain interior features of the stem 30.

The stem 30 has a vent 31, a connector portion 32, and a contact portion 33. An aperture or air passage 35 is provided in a portion 34 of the stem 30. The air passage 35 communicates or intersects with an air passage or aperture 36 made in the vent 31.

An aperture 37 is formed in the portion 32 of the stem 30 to slidably receive the disposable contact assembly. A portion or member 19 (see FIG. 1) occludes or blocks the aperture or passage 35 from the aperture 37.

The contact portion 33 may be provided with a transverse hole 38 and a threaded hole 39. The threaded hole 39 extends to hole 38 from the end of the contact portion 33. A screw 40 has a threaded portion 41, and screws into the hole 39 to retain a Vector Lead wire in the hole 38.

FIG. 4 illustrates a disposable contact electrode according to the instant invention. An electrode 50 includes a rod 51, a cup 52, and a conductive sponge 53. The rod 51 is preferably, but not essentially, provided with friction bump 54, adapted to retain the rod 51 in the aperture 37 of the stem 30. The rod 51 is attached to the cup 52. The cup 52 has walls 55 to retain the conductive sponge 53 which preferably, but not essentially, is made of a cellular material impregnated with a conductive material, of appropriate size to protrude from the cup 52.

In the preferred embodiment of the present invention, the cup 52 and the rod 51 are made of a conductive metallic material, but can also be made of a rigid plastic containing a dispersion of finely-divided conductive particles; or, alternatively, of a non-conductive material plated with a conductive metallic material.

In the preferred embodiment of the present invention, the cup 52 may be approximately one-half inch in diameter.

To use the present invention, a wire or conductor from an EKG machine may be inserted through the hole 38, and retained therein by tightening the screw 40. The bell 10 is held at its neck 14. The disposable contact 50 is grasped at the exterior of the cup 52, and the rod 51 is inserted into the aperture 37 of the stem 30.

The bulb 1 is squeezed to force air through apertures or passages 35 and 36 into the bell 10. The ring 20 is placed against the patient's skin, and the bulb 1 is released. This causes the air to flow from the bell 10 to the bulb 1, through apertures 35 and 36, creating a partial vacuum, drawing the bell 10 toward the patient's skin. In other words, the ring 20 is caused to collapse, forming an airtight seal between the bell 10 and the patient's skin, and drawing the sponge 53 against the patient's skin.

From the foregoing description, it can be seen that the present invention provides a Vector Lead device which is universally adaptable to all current EKG machines, and which eliminates the necessity of electrically-conductive jellies by providing a single disposable contact.

The contact of the Vector Lead device with the skin is improved by providing a soft pliable rubber ring 20 at its base.

The invention also provides a single contact pad of approximately one-half inch, thereby obviating the necessity of multiple sized "bells" while improving the quality of the EKG studies.

Furthermore, the single disposable contact is easy to manufacture, and results in less employee time and ancillary equipment in the performance of EKG's.

In a particular embodiment, the rubber bulb 1, has substantially a suction cup structure, and is of sufficient size to evacuate the air from the chamber of bell 10. This vacuum will pull the bell 10 against the skin, collapsing the rubber ring 20 which will bring the electrically-conductive pad 53 in contact with the skin.

The plastic bell 10 is approximately one inch in diameter and one and one-half inches in height with a heavy plastic collar 14 at its top. This heavy collar 14 will provide a firm base for the passage of the stem 30 which includes the air tube and the electrically-conductive contact. An integral part of this contact is the female connector 38 and the set screw 40 which in conjunction provide contact between the Vector Lead and the EKG terminal. This portion of the invention can be viewed in detail by reference to FIG. 3.

This contact passes through the dome of the bell 10 where there is a vent 31 to permit passage of air. It then terminates in a female connector 32 where the disposable contact 50 (FIG. 4) will plug in.

This disposable contact (FIG. 4) is composed of an electrically-conductive stalk or rod 51, approximately one-half inch long, with a soft plastic friction bump 54 at its distal end to be inserted in the female connector 32. The remainder of contact 50 is comprised of a plastic collar 55 to be grasped between the thumb and forefinger when inserting the contact, and the electrically-conductive sponge or pad 53 similar in nature to those currently used in disposable EKG leads.

The present invention thus provides an EKG Vector Lead apparatus having at its uppermost portion a hollow rubber bulb, at its center portion a plastic bell, and at its base a soft compressible rubber lip. The electrically-conductive components define a disposable contact unit in the approximate shape of a golf tee, having at one end an electrically-conductive pad, and at its other end a male connector. This unit is to be inserted in a female connector, permanently affixed to the bell, and having midway up its length a vent for air passage, and then to continue through the bell dome where it will divide at right angles into one portion with a female connector and set screw to adapt to current EKG common Vector terminals while the remaining portion furnishes the stem for connecting the rubber bulb.

With reference to FIGS. 1 and 2, the neck 2 is preferably, but not necessarily, fabricated from the same rubber the bulb is made of, but is thicker and will slip tightly over the air pipe or portion 34 to attain a seal therebetween.

The special ring 20, as illustrated best in FIG. 2, is critical to the proper functioning of the unit.

The section 21 should preferably be a firm rubber to assure that it adheres to the bell 10. The entire ring unit 20 is designed to be replaceable, and this heavier rubber section 21 will provide a "snap-off" connection.

The section 23 should consist of a thinner very pliable rubber allowing it to conform to body contours. The aperture 24 is hollow and air filled to allow the ring 20 to easily collapse when suction is applied to the bell 10.

It is contemplated that the vector lead apparatus according to the present invention may be provided in the form of an electrode kit. Such a kit includes, for example, a plurality of the bells 10, a plurality of the disposable contact members 50, at least one resilient bulb 1, at least one ring 20, and at least one stem 30.

Although the preferred embodiment of the present invention has been described, it will be understood that various changes may be made without deviating from the scope and spirit of the present invention as set forth in the appended claims.

I claim:

1. A medical instrumentation electrode apparatus, comprising:
   a substantially rigid and hollow vacuum bell, said vacuum bell being fabricated of electrically-insulating material;
   first means for creating a partial vacuum in said vacuum bell;
   second means for providing an air communication passage between said vacuum bell and said first means, said second means being selectively interconnectible between said vacuum bell and said first means;
   a contact member including a rod member having a cup member affixed to a lower end thereof, said rod member and said cup member being fabricated of substantially electrically conductive material;
   an electrically-conductive sponge member disposed at least partially within said cup member;
   an electrically conductive and substantially hollow stem member disposed within said vacuum bell selectively slidably receiving and holding at a lower end thereof said rod member such that said sponge member is disposed proximal to a lower open end of said vacuum bell;
   third means for selectively operably connecting said hollow stem member to an external medical instrument such that said sponge member is electrically connected to said external medical instrument via said electrically conductive stem member, said rod member, and said cup member;
   a substantially hollow resilient ring member secured coextensively around the periphery of said lower open end of said vacuum bell; and
   said ring member, when disposed adjacent an area of skin, is substantially collapsible upon evacuation of said vacuum bell, so as to bring said sponge member disposed proximal said lower end of said vacuum bell into contact with an area of skin.

2. A medical instrumentation electrode apparatus according to claim 1, wherein:
   said first means comprises a resilient bulb member;
   said second means comprises an upper end portion of said hollow stem member;
   said third means comprises a first electrically-conductive hollow branching portion provided on said hollow stem member;
   said hollow stem member is provided with a second hollow branching portion extending into the interior of said vacuum bell, said second hollow branching portion being disposed above said rod member received within said lower end of said hollow stem member; and
   said upper end portion and said second hollow branching portion of said hollow stem member are interconnected for forming an air passage therebetween.

3. A medical instrumentation electrode apparatus according to claim 2, wherein:
   an upper end portion of said vacuum bell is provided with a neck;
   said resilient bulb member is provided with a neck; and
   said upper end portion of said hollow stem member extends between said neck of said vacuum bell and said neck of said resilient bulb member so as to define an air communication passage extending from said resilient bulb member to said second hollow branching portion of said stem member which extends into the interior of said vacuum bell.

4. A medical instrumentation electrode apparatus according to claim 3, wherein:
   said first hollow branching portion of said stem member extends through a portion of said neck of said vacuum bell.

5. A medical instrumentation electrode apparatus according to claim 11, wherein:
   said third means further comprises a screw member threadedly received within a threaded end portion of said first hollow branching portion of said stem member;
   said first hollow branching portion of said stem member has an aperture disposed therein; and
   the inner end of said screw member disposed within said first hollow branching portion cooperates with said aperture of said first hollow branching portion to retain a vector lead wire of said external medical instrument received through said aperture of said first hollow branching portion.

6. A medical instrumentation electrode apparatus according to claim 1, wherein:
   said sponge member is fabricated of a substantially cellular material which is impregnated with an electrically conductive material.

7. A medical instrumentation electrode apparatus according to claim 1, wherein:
   said ring member is removably secured around a rim portion extending around the periphery of said lower open end of said vacuum bell.

8. A medical instrumentation electrode kit, comprising:
   a plurality of substantially rigid and hollow vacuum bells, each said vacuum bell being fabricated of electrically-insulating material;
   at least one first means for creating a partial vacuum in individual ones of said vacuum bells;
   second means for providing an air communication passage between individual ones of said vacuum bells and said first means, said second means being selectively interconnectible between individual ones of said vacuum bells and said first means;
   a plurality of disposable contact members, each said contact member including a rod member having a cup member affixed to a lower end thereof, said rod member and said cup member being fabricated of substantially electrically conductive material;
   an electrically-conductive sponge member disposed at least partially within said cup member of each of said disposable contact members;
   at least one electrically conductive and substantially hollow stem member for disposal within individual ones of said vacuum bells for selectively slidably receiving and holding at a lower end thereof a rod member of one of said disposable contact members such that said sponge member is disposed proximal to a lower open end of individual ones of said vacuum bells;

third means for selectively operably connecting said hollow stem member to an external medical instrument such that said sponge member is electrically connected to said external medical instrument via said electrically conductive stem member, said rod member and said cup member;

a substantially hollow resilient ring member secured coextensively around the periphery of said lower open end of each said vacuum bell; and said ring member, when disposed adjacent an area of skin, is substantially collapsible upon evacuation of said vacuum bell by said first means, so as to bring said sponge member disposed proximal said lower end of said vacuum bell into contact with an area of skin.

9. A medical instrumentation electrode kit according to claim 8, wherein:

said first means comprises a resilient bulb member;

said second means comprises an upper end portion of said hollow stem member;

said third means comprises a first electrically-conductive hollow branching portion provided on said hollow stem member;

said hollow stem member is provided with a second hollow branching portion adapted to extend into the interior of individual ones of said vacuum bells, said second hollow branching portion being disposed above said rod member when received within said lower end of said hollow stem member; and said upper end portion and said second hollow branching portion of said hollow stem member are interconnected for forming an air passage therebetween.

10. A medical instrumentation electrode kit according to claim 9, wherein:

an upper end portion of each said vacuum bell is provided with a neck;

said resilient bulb member is provided with a neck; and said upper end portion of said hollow stem member extends between said neck of said vacuum bell and said neck of said resilient bulb member when connected so as to define an air communication passage extending from said resilient bulb member to said second hollow branching portion of said stem member which extends into the interior of said vacuum bell.

11. A medical instrumentation electrode kit according to claim 10, wherein:

said first hollow branching portion of said stem member is adapted to extend through a portion of said neck of individual ones of said vacuum bells.

12. A medical instrumentation electrode kit according to claim 9, wherein:

said third means further comprises a screw member threadedly received within a threaded end portion of said first hollow branching portion of said stem member;

said first hollow branching portion of said stem member has an aperture disposed therein; and the inner end of said screw member disposed within said first hollow branching portion and said aperture of said first hollow branching portion cooperate to retain a vector lead wire of said external medical instrument received through said aperture of said first hollow branching portion.

13. A medical instrumentation electrode kit according to claim 8, wherein:

said sponge member is fabricated of a substantially cellular material which is impregnated with an electrically conductive material.

14. A medical instrumentation electrode kit according to claim 8, wherein:

said ring member is removably secured around a rim portion extending around the periphery of said lower open end of each said vacuum bell.

* * * * *